United States Patent [19]

Meyer et al.

[11] Patent Number: 4,596,561
[45] Date of Patent: Jun. 24, 1986

[54] PREFILLED SINGLE-DOSE SYRINGE

[75] Inventors: Gabriel Meyer; Ernst Howald, both of Vesenaz, Switzerland

[73] Assignee: Meditec S.A., Luxembourg, Luxembourg

[21] Appl. No.: 688,028

[22] PCT Filed: May 1, 1984

[86] PCT No.: PCT/CH84/00065
§ 371 Date: Dec. 31, 1984
§ 102(e) Date: Dec. 31, 1984

[87] PCT Pub. No.: WO84/04252
PCT Pub. Date: Nov. 8, 1984

[30] Foreign Application Priority Data

May 4, 1983 [CH] Switzerland ................. 2416/83

[51] Int. Cl.$^4$ ............................................. A61M 5/00
[52] U.S. Cl. ................................................. 604/190
[58] Field of Search ............... 604/218, 238, 236, 190, 604/240, 241, 231, 89; 128/766

[56] References Cited

U.S. PATENT DOCUMENTS 3,159,159 12/1964 Cohen .............................. 128/766
4,061,143 12/1977 Ishikawa ........................... 604/190
4,365,626 12/1982 House .

FOREIGN PATENT DOCUMENTS 0111796 12/1983 European Pat. Off. .
0112574 12/1983 European Pat. Off. .
2401782 7/1974 Fed. Rep. of Germany ...... 604/190
2361121 of 0000 France .

OTHER PUBLICATIONS

"Glass Embolism", published in The Lancet, Dec. 16, 1972.
"Glass Particles in Intravenous Injections", published in The New England Jrnl. of Medicine, Dec. 7, 1972.
"Residues in Antibiotic Preparations: I. Scanning Electron Microscopic Studies of Surface Topography", published in American Journal of Hospital Pharmacy, May 1976.
"Particulate Contamination in Intravenous Fluids: Nature, Origin, and Hazard", published in Pharmaceutical Journal, Mar. 3, 1973.
"Foreign Bodies in Contrast Media for Angiography", published in American Journal of Hospital Pharmacy, vol. 34, Jul. 1977.
"Coring of Rubber Closures", published in The Pharmaceutical Journal, No. 224, Feb. 1980.
"A Foreign Matter Affair: The Problem of Particulates", published in The American Journal of Intravenus Therapy.

Primary Examiner—John D. Yasko
Attorney, Agent, or Firm—Lerner, David, Littenberg, Krumholz & Mentlik

[57] ABSTRACT

The prefilled single-dose syringe 10 in the application features a barrel 11 provided with an narrowed-diameter portion 27 or neck and a rim surrounding its opening; a nozzle 12 equipped with finger stubs and a needle-carrying ferrule 13 transpierced by an axial channel 31; and a stoppering device 23 featuring an elastomer stoppering cork mounted at the end of a bracing ferrule that is attached to the bottom of the nozzle. This lower end of the bracing ferrule fits onto a collar, in the shape of a truncated cone, that is part of the bottom of the nozzle. This collar serves as a support for a membrane microfilter 28, which is pressed between the opposing surfaces of the bracing ferrule and the filter-carrying ferrule.

16 Claims, 11 Drawing Figures

PREFILLED SINGLE-DOSE SYRINGE

BACKGROUND OF THE INVENTION

The present application concerns a prefilled single-dose syringe featuring a barrel open at at least one of its ends and provided with a narrowed-diameter portion neighboring this end; a stoppering device fitted into the barrel to stopper said narrowed-diameter portion, which stoppering device is movable axially between a first position, called the storage position, and a second position, called the injection position, and featuring an internal tube; and a nozzle attached to this stoppering device, fitted onto the shank of the open end of the barrel and provided with a ferrule equipped with an axial channel, which axial channel is intended to communicate with the internal tube of the movable stoppering device when it is moved into its second position.

There already exist a large number of prefilled syringes that are made up of a body or barrel containing the medicine to be injected into the patient, a movable plunger inside of this barrel, a needle attached to one of the ends of the barrel, and a cap that protects the barrel and ensures its airtightness. Such an existing device is illustrated, for example, by Swiss Pat. No. 571 858. It is currently still used a great deal because it does not require decanting and because the single dose is guaranteed by the manufacturer.

However, even if the syringe should, in principle, be thrown away, it remains reusable, and there is nothing to guarantee, if not for a tamper-proof original packaging, that the syringe contains a proper medicine. The fact that the airtightness is ensured by the cap, which contains air, constitutes another disadvantage of this device. Furthermore, the ampul requires costly testing after filling and after the plunger is put in place.

To overcome these various drawbacks was proposed a syringe of the ampul-syringe type, described in European Patent Application No. 83112127.2 filed by the applicant, regarding a barrel containing a medicine under pressure, the opening of which is stoppered by a stoppering device that forms a unit with a nozzle, equipped with an attachment ferrule, an injection needle, and a tube capable of putting the interior of the body of the syringe in communuication with the needle; both the nozzle and the stoppering device attached to it are movable between a stoppered position and an in-use position.

This principle of stoppering by means of a nozzle could have been adapted for a syringe of a different type, comprising a body and a plunger to slide axially inside the body, as well as for a double-compartment syringe or mixing syringe that consists of two plungers serving two chambers containing, initially, two different respective products intended to be mixed before they are injected. This latter device, for example, is described in the applicant's European Patent Application No. 83113098.4.

The manual or automatic testing mentioned earlier of ampuls containing medicines to be injected, with the intention of detecting the possible presence of solid particles in the medicine contained in the ampul, proves to be relatively costly for the manufacturer. This testing is responsible for a not negligible precentage of the production costs of the product, due to the fact that it requires a testing station, the installation and operating costs of which are high.

In addition, the losses due to unacceptable finished products have a negative influence on the cost price of sales of acceptable products.

Although this testing, performed by the manufacturer at great expense, theoretically permits the arrival at a product that is considered acceptable—that is, of which at least 90% or 95% is greater than 50 micrometers—free of any solid particles, the practical reality is quite different because storage, on the one hand, and the manipulations required before using the product, on the other, may alter its quality considerably. In effect, during storage certain products may produce solid deposits, which are not entirely dissolved after shaking prior to injection. In the mixing syringes, the powder of freeze-dried medicines is not always dissolved completely by the solvent in such a way that the risk of injecting solid residues is not nonexistent. When the medicine is contained in an ampul the neck of which must be broken to free the product, very small particles of broken glass are often mixed in with the liquid to be injected.

When the medicine is in a container stoppered by a rubber cork that must be pierced with a needle before removing or injecting the liquid medicine, particles of synthetic material, especially elastomers, may be found in the liquid and risk being injected into the patient's body.

The problems cited above are well known by the specialists, but until now no completely satisfactory solution has been found—that is, a solution that permits both elimination of the expensive testing by the manufacturer and, at the same time, elimination of the risk of injecting solid particles into the patient's body.

The article "Glass Embolism", published in the journal *The Lancet* of Dec. 16, 1972, page 1300, raises the problem of particles of cotton, rubber, synthetic materials, glass, or other solid matter present in doses for intravenous injection; mentions the clinical consequences likely to be provoked in the patient; and proposes a solution, consisting of performing the filling of the containers in a pressure chamber.

The article "Glass Particles in Intravenous Injections", published in the periodical *The New England Journal of Medicine* of Dec. 7, 1972, page 1204, raises the problem of the introduction of glass particles into the human body during intravenous injections and suggests filtering the medicine by means of a filtration device marketed by the company Millipore. This device involves a filtering insert comprised of a housing containing a filtering membrane and supplied with an entry mouthpiece and an exit ferrule arranged on both sides of the membrane. This insert is intended to be mounted between a syringe and the injection needle in such a way that the liquid to be injected must pass through a filtering membrane. Its cost very often constitutes an obstacle to its general use. Furthermore, even if its use is recommended, putting it in place may be intentionally or unintentionally omitted by the health care personnel.

Finally, because this insert is intended to be used with any syringe containing any medicine to be injected, it must meet very broad criteria, especially to adjust to difference in volume and to different viscosities and to be compatible with all medicines of any kind.

The article "Residues in Antibiotic Preparations: I. Scanning Electron Microscopic Studies of Surface Topography" published in the periodical *American Journal of Hospital Pharmacy* (vol. 33) of May 1976, pages 433–443, treats the problem of the pathological consequences of the injection of solid particles present in antibiotic solutions supposed to be pure according to pharmaceutical standards.

The article "Particulate Contamination in Intravenous Fluids: Nature, Origin, and Hazard", published in the periodical *Pharmaceutical Journal* of Mar. 3, 1973, also analyzes the clinical consequences of the injection of particles with medicines injected intravenously.

The article "Foreign Bodies in Contrast Media for Angiography", published in the periodical *American Journal of Hospital Pharmacy* (vol. 34) of July 1977, pages 705-708, describes the analysis work performed on liquids intended for intra-arterial injections for radiological examinations, analyses that revealed the presence of contaminating particles, especially tiny glass fragments of a diameter ranging from 0.5 micrometers to 450 micrometers. The author concludes by saying that these foreign particles must be eliminated as much as possible.

The article "Coring of Rubber Closures", published in the periodical *The Pharmaceutical Journal* (no. 224) of Feb. 1980, page 120, raises the problem of the presence of particles of rubber in solutions to be injected. The author estimates that these particles generally originate from the technique of piercing the stopper corks of ampuls containing the products and points out that the consequences on the circulatory system of the patient are still not well known.

The article "A Foreign Matter Affair: The Problem of Particles", published in the periodical *The American Journal of Intravenous Therapy*, pages 23-32, summarizes the experiments that had been performed on animals to analyze the clinical consequences of the injection of solid particles of cotton, glass, rubber, synthetic matter, etc., into the vascular system. The author concludes the article by pointing out that there are numerous cases of contamination and that despite the measures already undertaken, technical progress is essential to try to bring the effective purity of injected medicine as close as possible to 100%.

All these articles in the medical literature clearly demonstrate that the presence of solid particles of any kind in injectable medicines constitutes a not-to-be neglected danger to the ill person and that at present no economically visable means has permitted the elimination of this risk without exaggeratedly increasing the cost of the treatment given.

The present application proposes to alleviate the drawbacks mentioned above by proposing a system that permits the elimination of the costly traditional testing performed by the manufacturer; avoids any contamination of the medicine to be injected by solid particles of glass or rubber usually introduced during the manipulations preceding injection; and guarantees the absence in the liquid actually injected of any air bubble or any solid particle of whatever origin, the diameter of which is larger than a specific size.

To this end, the syringe in this application is distinguished by the fact that it features at least one membrane microfilter inserted between the internal tube of the movable stoppering device and the axial channel of the ferrule of the nozzle connected to this movable stoppering device.

One could object that there already exist syringes containing a filter, such as, for example, those covered by U.S. Pat. No. 4,365,626. These syringes are, in fact, comprised of an ampul, the ends of which are stoppered by two elastomer corks, and a needle-carrying ferrule equipped with a double needle, one of which is intended for piercing one of the stopper corks of the ampul, and a filter, the intention of which is to catch particles of rubber ripped away when the cork is pierced. However, it is to be noted that the filter is of a piece with the needle-carrying ferrule mounted on the ampul just before the syringe is to be used; that it is, by this fact, an accessory element that could perhaps be replaced by another needle not equipped with a filter; and that it does not fulfill its role with repect to a total guarantee of an absence of solid particles in the liquid to be injected cited above. Moreover, the filter described—housed in a complex support structure that also carries the needle that pierces the stopper cork—is essentially intended to eliminate contamination that arises during this piercing. Finally, in light of the number of parts making up the system, the cost of production of the syringe described is so high that there could be no question of applying it as a universal system for the industrial nations and certainly not adaptable to the medical conditions encountered in certain economically disadvantaged nations.

One could also object that there exist syringes equipped with a so-called in-depth filter, such as those covered by the French Patent issued under No. 2, 361 121, comprising a syringe body provided with a plunger and stoppered at one end by a stoppering device. The needle-carrying nozzle is equipped with a deep filter intended, as before, to catch particles that might have been torn away from the elastomer membrane during its piercing.

The in-depth filters are usually made of a kind of pad made out of a variety of material, such as, for example, sintered metal or some other suitable material, which provides a collection of microtubules, the width of which is deemed to be sufficiently narrow to catch undesirable solid particles. Nevertheless, in-depth filters do not permit guaranteeing a lower limit of filtration of 100%. Actually, if statistical trials permit confirmation that such type of in-depth filters filter out, for example, 80% of particles with a diameter equal to or greater than 50 micrometers, this does not exclude the possibility that several paraticles of much larger diameter—for example, particles measuring 150 micrometers—might find their way through and ultimately find their way into the filtered liquid.

The membrane microfilters, on the other hand, permit absolute means of guaranteeing 100% filtration of any solid particles the diameter of which is greater than the nominal diameter of the pores of the filter. The diameter of the pores is established by the manufacturer and can be verified by the existing techniques called "bubble point". The membrane microfilter is the equivalent of a strainer, all the openings of which are identical and determined by its construction.

In a preferred design, the membrane microfilter of the prefilled syringe in this application has pores the largest diameter of which is between 0.2 and 5 micrometers. The materials used for the manufacturer of this microfilter are preferably selected from the following substances: polyamides, acrylic copolymers covered with nonwoven polyamide, cellulose esters, polytetrafluorethylene, polypropylenes.

BRIEF DESCRIPTION OF THE DRAWINGS

The present invention can be better understood by referring to the description of the various variants and to the attached drawings, in which.

DESCRIPTION OF A PREFERRED EMBODIMENT

Figure 1:
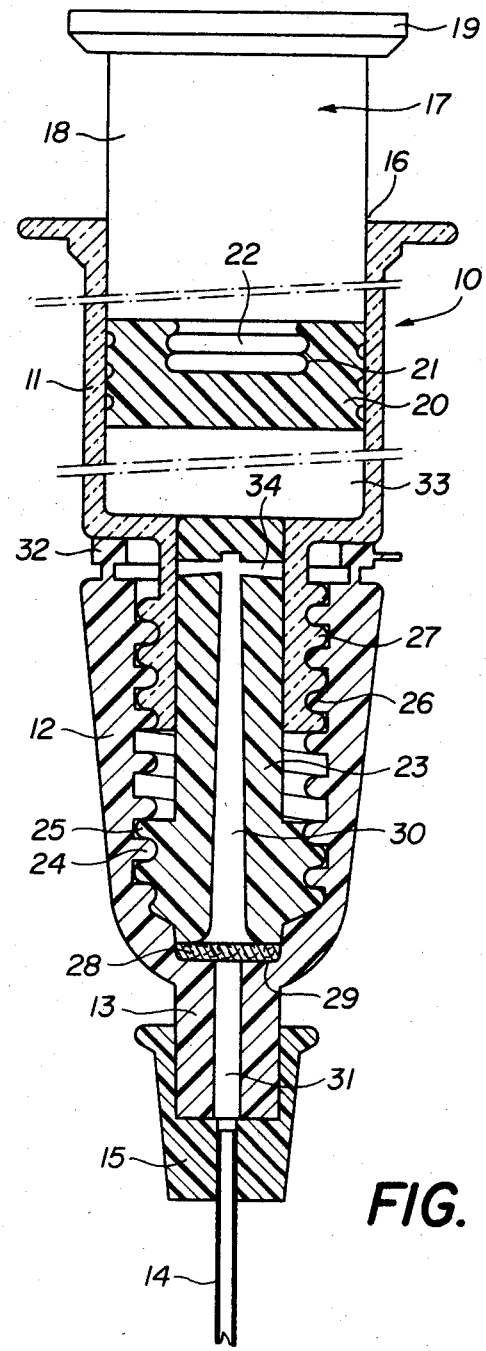
FIG. 1 shows a cross section of a syringe with plunger, as in the invention.

In reference to FIG. 1, the syringe 10 shown comprises a barrel 11, a nozzle 12 that is fitted to the lower end of the barrel 11 and equipped with a ferrule 13 for the attachment of an injection needle 14, partially illustrated, carried by needle-carrier 15 mounted on the ferrule 13. The barrel 11 of the syringe, in this case, features an upper opening 16 transpierced by a plunger 17 made up of a plunger shaft 18, a thumbpiece 19, and the plunger itself 20. The plunger 20 features in the center of its upper surface a hollow 21 that fits into a fluted ferrule 22 attached to the lower end of the plunger shaft 18 to make the connection between the plunger shaft 18 and the plunger 20. It is obvious that the barrel 11, open at both its ends, could be replaced by a barrel stoppered at its upper end in which the single dose of medicine is contained under pressure. The narrowed-diameter portion or neck 27 of the barrel is stoppered by a movable stoppering device 23 that forms a unit with the nozzle 12 by screwing on or any other appropriate means of attachment. For this purpose the nozzle features threading 24 designed to correspond to a matching threading 25 on the base of the stoppering device 23.

The nozzle 12 has the general shape of a hood, the interior wall of which features threading 26 that permits its screwing onto the threaded neck 27 of the barrel 11 of the syringe. Between the lower end of the movable stoppering device 23 and the bottom of the nozzle 12 is fitted a membrane microfilter 28 held in place by a bolster 29 and inserted between the internal tube 30 of the stoppering device 23 and the axial tube 31 crossing the ferrule 13 and connecting to the injection needle 14. The membrane microfilter is appropriately designed to catch all particles of a diameter greater than 2 micrometers. A locking device 32, made up, in this case, of a strip that is attached to the upper rim of the nozzle 12, locks this nozzle, with regard to the barrel 11, in its stoppered position, as shown in the figure. In this position, the medicine is contained in the chamber 33 of the barrel 11. This chamber is closed at its base by the stoppering device 23.

It is to be noted that the stoppering device 23 is connected to the nozzle 12 and that the membrane microfilter 28 is permanently attached between the base of the stoppering device and the bottom of this nozzle. The membrane microfilter 28 is not in contact with the medicine during storage of the syringe.

When the care-giver wants to inject the patient with the medicine, he tears off the locking strip 32 and screws the nozzle 12 as far as it will go on the neck of the barrel 11 of the syringe; this has the effect of forcing the stoppering device 23 into the chamber 33 to such an extent that the mouthpieces of the T-shaped cross branch 34 of the internal tube 30 are located inside this chamber. The medicine can run through this tube and of necessity through the membrane microfilter 28 and flow through the axial channel 31 into the injection needle 14, under the force exerted by the plunger 20.

Figure 2:
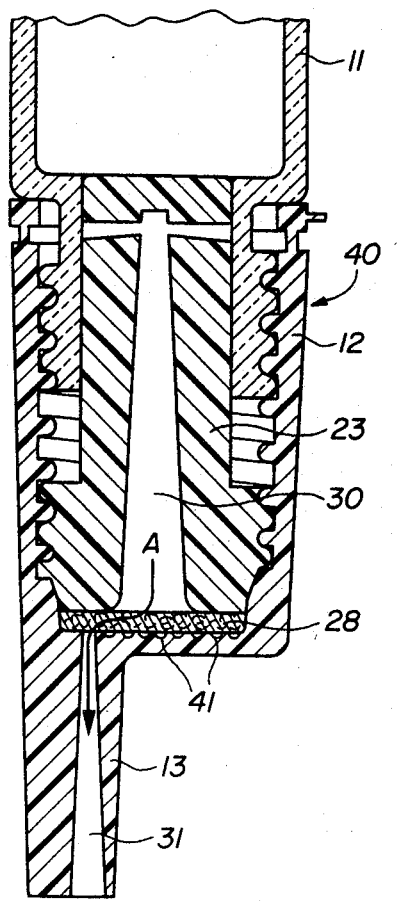
FIG. 2 shows a partial cross section of a first variant of a syringe with plunger as shown in FIG. 1.

FIG. 2 partially shows a syringe 40, the configuration of which is practically identical to that of FIG. 1. Like the preceding figure, it features a barrel 11 as well as a nozzle 12 containing a stoppering device 23.

In this example, the ferrule 13 is off center in such a way that the axial channel 31 is no longer, as in the preceding example, arranged as the extension of the internal tube 30 that traverses the stoppering device 23. In this case the membrane microfilter 28 has, in addition to its usual filtering role, the function of connecting the two tubes 30 and 31 to permit the follow of the medicine originally contained in the barrel 11 of the syringe 40, in the direction of the arrow (A). To permit the flow of filtered liquid in the direction of the axial channel 31, the bottom of the nozzle is supplied with a series of drainage grooves 41 that collect the liquid and direct it toward the channel 31.

Figure 3:
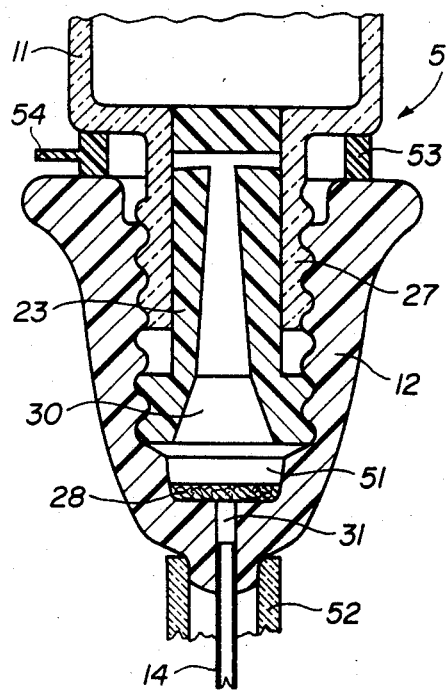
FIG. 3 shows a partial view of a syringe as in the invention illustrating, basically, its nozzle equipped with a filter and a locking device.

FIG. 3 shows a partial view of a prefilled single-dose syringe 50 featuring, as before, a barrel 11 and a nozzle 12 screwed onto the neck 27 of the barrel 11 that is provided with a stoppering device 23 equipped with a T-shaped internal tube 30.

In this example, the membrane microfilter 28 lies loose in a cavity 51 at the base of the nozzle 12. Below the membrane microfilter 28 begins the axial channel 31, which is, in this case, designed to receive directly the upper end of an injection needle 14, glued or attached by any other appropriate means and protected by a tubular cap 52 that fits over a ferrule of the nozzle 12.

The membrane microfilter 28 is appropriately made of a material having approximately the same melting point as the material of the nozzle 12, as this permits a peripheral welding of said filter to the bottom of the nozzle.

The locking mechanism, intended to lock the nozzle in its initial stoppered position, consists, in this case, of a ring 53 that is added, which is to say that it is not directly attached to the nozzle. This ring 53 may be made of a strip folded over into a ring, the ends of which are attached to each other by welding, clipping, gluing, etc. This added ring 53 could also be replaced by a strip attached to or connected by anchoring points to the nozzle 12. It could also be provided with a tear strip 54.

As before, the membrane microfilter 28 is directly connected to the movable stoppering device 23-nozzle 12 unit and is inserted between the internal tube 30 and the axial channel 31.

Figure 4:
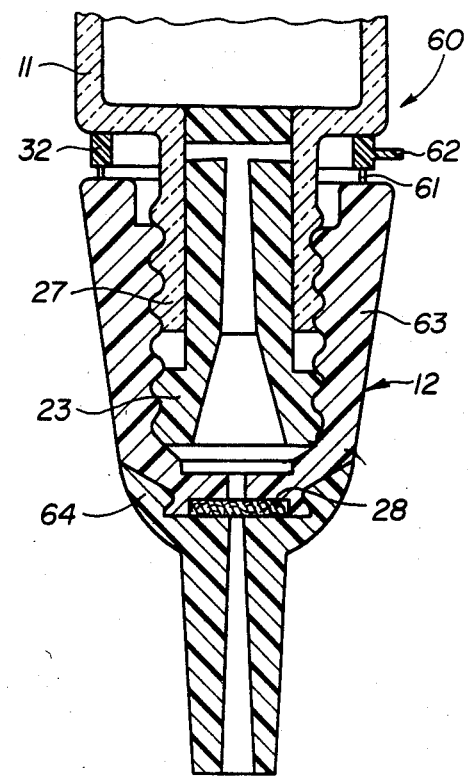
FIG. 4 shows a variant of the syringe shown in FIG. 3.

FIG. 4 illustrates a syringe 60 equipped with a barrel 11 and a nozzle 12 screwed onto the neck 27 of the barrel. The nozzle 12 features a stoppering device 23 identical to that of the syringe 50 shown in FIG. 3. A strip 32 attached to the upper rim of the nozzle 12 by anchoring points 61 and provided with a tear strip 62 serves as the locking device and locks the nozzle 12 in its stoppered position.

In this example, the nozzle 12 is actually made up of two interlocking components 63 and 64 assembled at the time of assembly. A membrane microfilter 28, located in a hollow specially designed for it, is pressed between the two components 63 and 64. This microfilter 28 is of necessity traversed by the medicine as it is injected.

Figure 5:
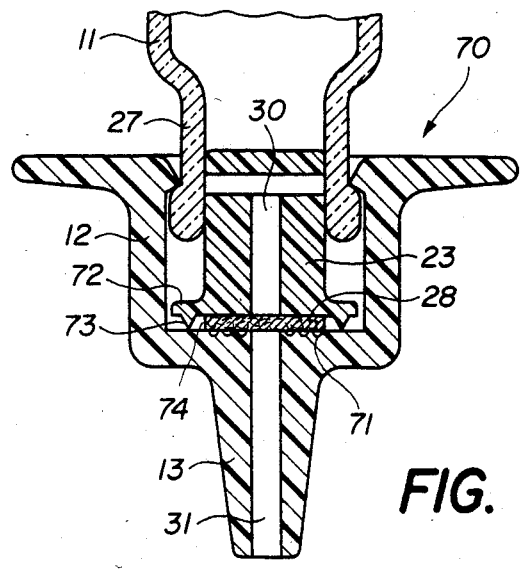
FIG. 5 shows another design in which the medicine to be injected is contained in a barrel under pressure.

FIG. 5 illustrates another design of the prefilled single-dose syringe 70 featuring a barrel 11 made up of an ampul, made of glass or synthetic material, closed at its upper end; a nozzle 12; and a stoppering device 23 fitted into the neck 27 of the barrel 11. The nozzle 12 is provided with a needle-carrying ferrule 13 crossed by an axial channel 31 logically positioned as the prolongation of the internal tube 30 of the stoppering device. A membrane microfilter 28 is inserted between the internal tube 30 and the axial channel 31. A drainage grid 71 covers the bottom of the nozzle to facilitate the follow of filtered liquid medicine.

In this example, the stoppering device 23 features a ring-shaped rim 72 provided with a protuberance 73, clearly triangular in cross section, intended to rest in a ring-shaped hollow 74 cut into the bottom of the nozzle 12. This arrangement permits the welding of the stoppering device 23 to the nozzle 12 by means of a sonotrode to hold the filter in position and to ensure the airtightness around this filter in such a way that the liquid originally contained in the barrel must of necessity pass through the membrane microfilter 28.

On the other hand, given that the membrane microfilter is impermeable to gas when it is wet and when this gas is at a pressure less than the bubble point of this filter, the medicine to be injected may be stored inside the barrel under pressure such that at the end of the injection, the gas remains at a pressure less than this bubble point so that there is no risk of injecting it into the tissue of the patient.

Figure 6:
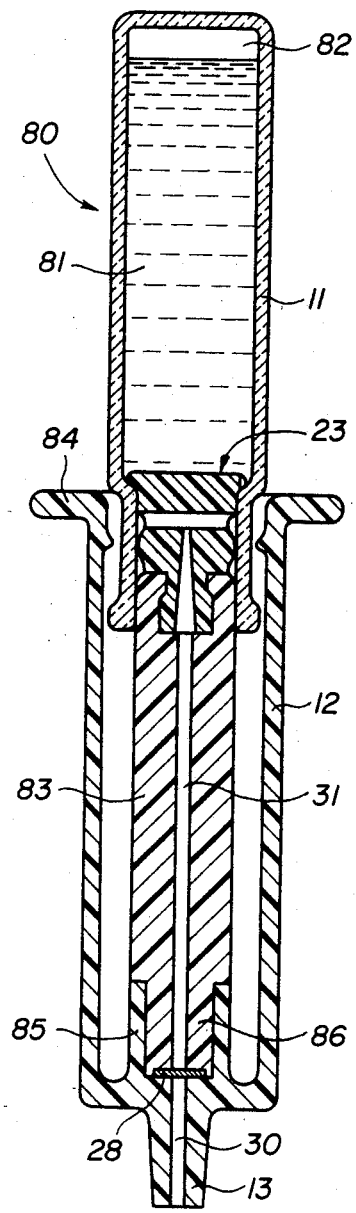
FIG. 6 shows another design in which the medicine to be injected is contained in a barrel that is closed at one end, the stoppering device serving as a plunger.

FIG. 6 shows another design of a prefilled syringe 80 with a single dose 81 contained in a barrel 11 under the very light pressure of a gas 82. The barrel 11 is stoppered by a stoppering device 23 mounted at the open end of a shaft 83 that forms a unit with the bottom of the nozzle 12 and is provided at its upper end with two flanges 84. The attachment of the stoppering device 23 at the end of the shaft 83 may be done in any manner, as long as this attachment is rigid during use of the syringe. To permit the placement of the membrane microfilter 28, the base of the nozzle 12 is provided with a ring-shaped collar 85 into which fits a slightly conical nipple 86 forming the lower end of the shaft 83. As in the preceding examples, the membrane microfilter 28 is inserted between the internal tube 31 of the stoppering device 23 and the axial channel 31 of the needle-carrying ferrule 13.

In this syringe, the stoppering device plays the role of the plunger when the user pushes on the bottom of the barrel to force the latter in the direction of the nozzle.

Figure 7:
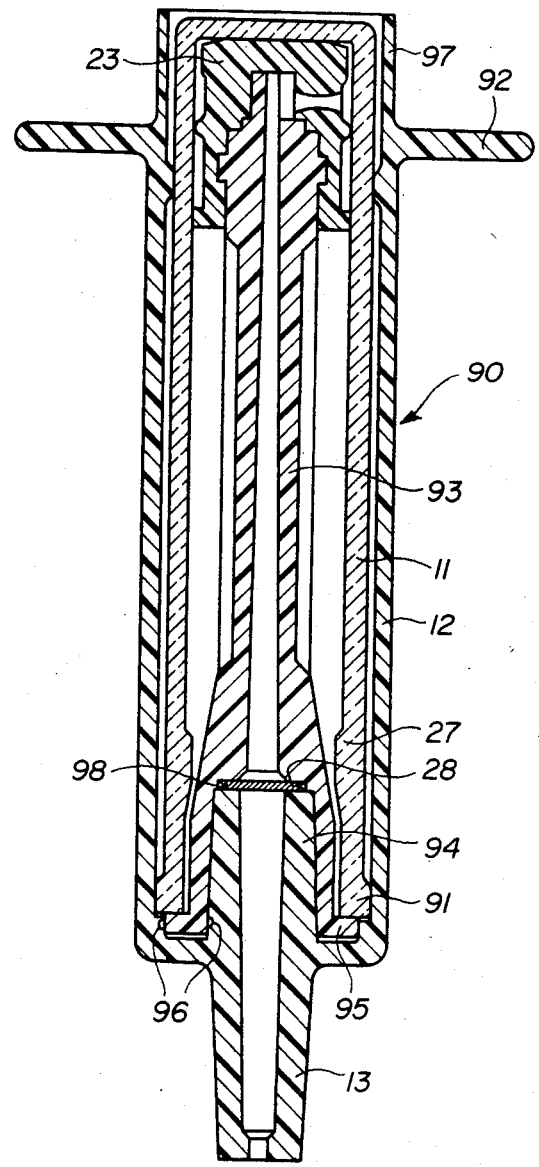
FIG. 7 illustrates a variant of the system in FIG. 6.

A variant of this device is illustrated by FIG. 7, which shows the syringe 90 in its postinjection position. It features a barrel 11 provided with a narrowed-diameter portion or neck 27 and a rim 91 around its opening; a nozzle 12 equipped with finger stubs 92 and a needle-carrying ferrule 13 transpierced by an axial channel 31; and a stoppering device 23 featuring, in fact, an elastomer stoppering cork mounted at the end of a bracing ferrule 93 that is attached to the bottom of the nozzle 12 by any appropriate means. In the example shown, the lower end of the bracing ferrule 93 fits into a collar 94, in the shape of a truncated cone, that is part of the bottom of the nozzle 12. This collar serves as a support for the membrane microfilter 28, which is pressed between the opposing surfaces of the bracing ferrule 93 and the filter-carrying collar 94. The ring-shaped rim 95 of the bracing ferrule 95 can be attached to the bottom of the nozzle 12 simply by screwing, but it can also include a cog 96 that fits into a corresponding ring-shaped groove cut into the collar 94.

As this figure clearly shows, when the barrel 11 is pushed completely into the nozzle 12, its bottom becomes flush with the ring-shaped rim 97 of the upper end of the nozzle 12; this ensures that it cannot be reused, due to the fact that it is impossible to extract the barrel to return it to its original position without damaging the system.

This design constitutes a complement to the postinjection neutralization provided by the membrane microfilter, which when wet prevents any entry of air, and consequently, any return of the barrel to its original position.

To provide better retention of the membrane microfilter on the filter-carrying collar 94, this latter can be provided with points 98 intended to press the filter and prevent any escape of liquid due to the capillarity of the liquid medicine.

The rim 95 may also have a different shape, adapted to the corresponding shape of the inner wall of the nozzle, especially any shape lending itself to welding by sonotrode.

Figure 8:
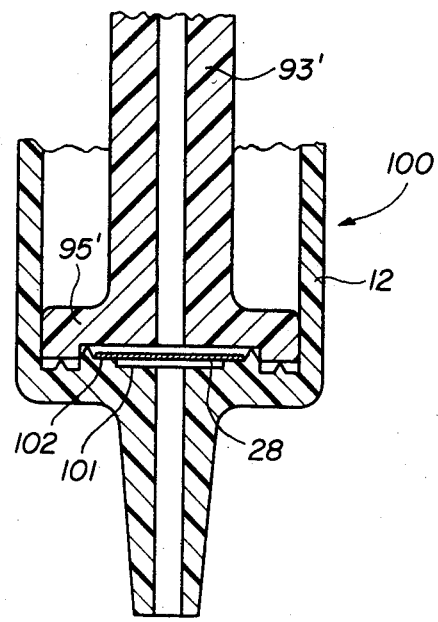
FIG. 8 illustrates another means of attaching the bracing ferrule of the system in FIG. 7.
Figure 9:
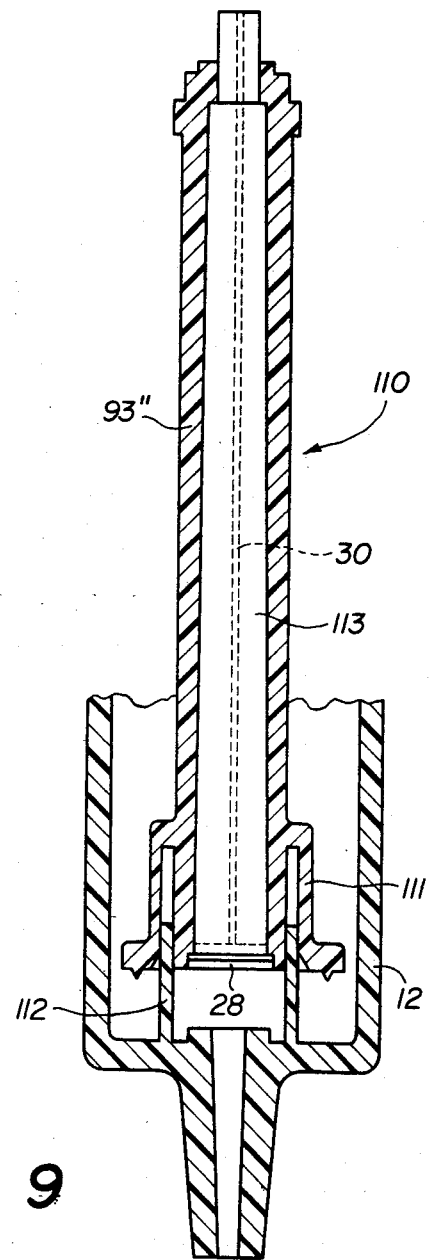
FIG. 9 shows a variant of the design in FIG. 8.
Figure 10:
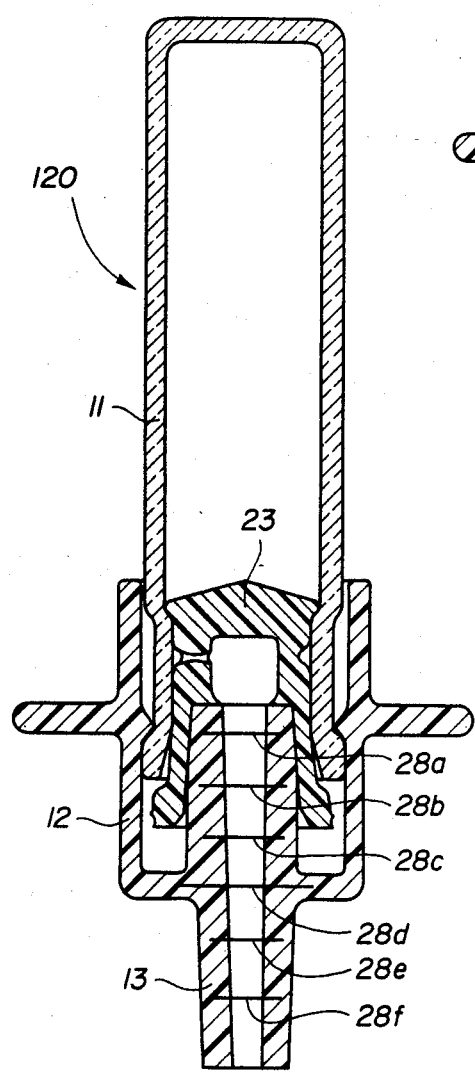
FIGS. 10 and 11 illustrate different possibilities for mounting the filter by a process of superinjection.

All sorts of variants can be imagined, especially those illustrated by FIGS. 9 and 10. In the example of the syringe 100 partially illustrated in FIG. 8, the bracing ferrule 93' features a ring-shaped rim 95' intended to be attached by ulrasound welding to the bottom of the nozzle 12. The membrane microfilter 28 is contained in a hollow 101 located between the base of the bracing ferrule 93' and the bottom of the nozzle 12 and is pressed around its periphery between the ring-shaped rim 95' and a flange 102 located in the bottom of the nozzle. This technique permits ensuring perfect airtightness and retention of possible loose fibers of the filter.

In the example of the syringe 110 partially illustrated in FIG. 9, the bracing ferrule 93" features a bell-shaped base 111 that fits onto a ring-shaped collar 112 that is part of the bottom of the nozzle 12. The bracing device contains a core 113 traversed by the internal tube 30, and its lower end supports the membrane microfilter 28. The filter is sandwiched between two opposing flat surfaces when the bell 111 is fitted onto the collar 112. The bell 111 may feature a ring-shaped rim intended to be welded to the bottom of the nozzle 12.

In the foregoing examples, the membrane microfilter 28 has always been positioned between two parts manufactured separately, then assembled by various techniques. The technique of superinjection permits the placing of this filter at any location transversal to the internal tube 30 or the axial channel 31.

FIG. 10 partially illustrates a prefilled single-dose syringe 120 in which the liquid to be injected is contained in a pressurized-gas barrel (not shown). The possible positions for the membrane microfilter are indicated by the references 28a, 28b, 28c, 28d, 28e, 28f. The cutout filter in the injection device is held by two rods. It is integrated by superinjection with the bracing ferrule of the stoppering device 23, which forms a unit with the nozzle 12, or with the needle-carrying ferrule 13, also forming a unit with the nozzle 12.

Figure 11:
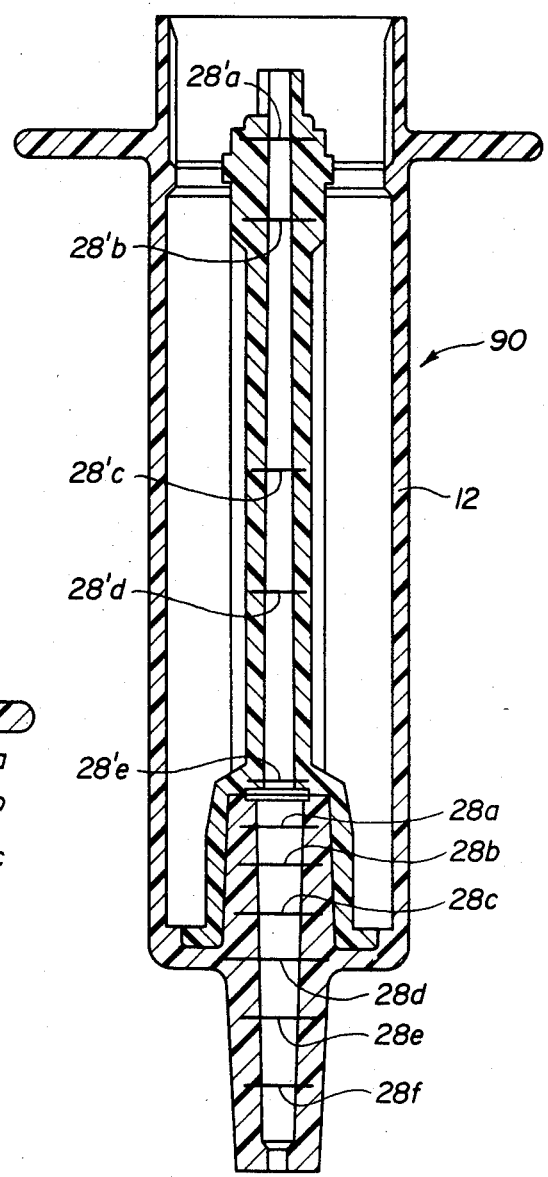

FIG. 11 partially illustrates the prefilled single-dose syringe 90 identical to that described in reference to FIG. 8. The references 28a, 28b, 28c, 28d, 28e, 28f represent, as before, the possible positions of the membrane microfilter 28, integrated with the collar 94 by a moulding process. The references 28'a, 28'b, 28'c, 28'd, 28'e, 28'f indicate possible positions of the membrane microfilter 28 integrated with the bracing ferrule by moulding.

It is to be noted that in all the variants described, the membrane microfilter has a useful surface smaller than the narrowest diameter of the barrel. In practice, the filtering material used to make the membrane microfilter and the selection of the diameter of its pores are determined by the type, the viscosity, and the volume of the medicine contained in the barrel, which permits the filter to be adapted to the medicine in an absolutely specific—therefore economical and profitable—manner.

Other variants could be imagined. However, it is essential that the construction of these syringes lend itself to simple manufacturing, with automatic assembly of all the components.

We claim:

1. Prefilled single-dose syringe, comprising:
an ampoule open at at least one of its ends and provided with a narrowed-diameter portion neighboring said open end;
a stoppering device fitted into said ampoule to stopper said narrowed-diameter portion, which stoppering device is movable axially between a first storage position and a second injection position, and featuring an internal conduit communicating with said ampoule when said stoppering device is moved into its second position;
a capsule attached to said stoppering device and fitted onto the shank of said open end of said ampoule, said capsule provided with a tip adapted for carrying a needle and having an axial channel, which axial channel is intended to communicate with said internal conduit of said movable stoppering device when it is moved into its second position; and
at least one membrane microfilter fixed permanently within the syringe between the lower end of said movable stoppering device and the bottom of the capsule so that the fluid to be injected is in contact with said microfilter only when said stoppering device is in said injection position.

2. Syringe as in claim 1, distinguished by the fact that the membrane microfilter features pores with a maximum diameter of between 0.2 and 5 micrometers.

3. Syringe as in claim 1, distinguished by the fact that the membrane microfilter is made of a substance selected from the following groups: polyamides, acrylic copolymers coated with nonwoven polyamide, cellulose esters, polytetrafluorethylene, polypropylenes.

4. Prefilled single-dose syringe featuring a barrel open at at least one of its ends and provided with a narrowed-diameter portion neighboring said open end; a stoppering device fitted into said barrel to stopper said narrowed-diameter portion, said stoppering device being movable axially between a first storage position and a second injection position, said stoppering device having an internal tube; a nozzle attached to said stoppering device and fitted onto the shank of said open end of said barrel and provided with a ferrule equipped with an axial channel, said axial channel intended for communication with said internal tube of said movable stoppering device when said stoppering device is moved into its second injection position; and at least one membrane microfilter pressed between the lower end of said stoppering device and the bottom of said nozzle.

5. Syringe as in claim 4, distinguished by the fact that the membrane microfilter is housed in a hollow cut into the bottom of the nozzle and that it is attached to this bottom by gluing or welding.

6. Syringe as in claim 4 or 5, distinguished by the fact that the membrane microfilter and the nozzle are made of materials having approximately the same melting point and that the filter is attached to the bottom of the nozzle by peripheral welding.

7. Syringe as in claim 4, distinguished by the fact that the membrane microfilter is pressed between the end of the nozzle and a nonmovable needle-carrying ferrule.

8. Syringe as in claim 4, in which the stoppering device is made up of an elastomeric stoppering head and a bracing ferrule, distinguished by the fact that the membrane microfilter is located between the end of the bracing ferrule and the bottom of the nozzle.

9. Syringe as in claim 8, distinguished by the fact that the membrane microfilter is pressed between the bracing ferrule and the bottom of the nozzle.

10. Syringe as in claim 8 in which the bracing ferrule is welded to the bottom of the nozzle, distinguished by the fact that the membrane microfilter is housed in a hollow cut between the bracing ferrule and the bottom of the nozzle and that the membrane microfilter is pressed between a flat, ring-shaped rim of the bracing ferrule surrounding said hollow and a ring-shaped protuberance of the bottom of the nozzle.

11. Syringe as in claim 8, distinguished by the fact that the bottom of the nozzle features a ring-shaped collar, at the bottom of which the membrane microfilter is placed, and that the bracing ferrule features a slightly conical nipple that fits into said collar.

12. Syringe as in claim 8, distinguished by the fact that the nozzle features a collar in the shape of a truncated cone located in the extension of the needle-carrying ferrule of the nozzle, that the bracing ferrule features a base shaped like a bell that fits over said collar in the shape of a truncated cone, and that the membrane microfilter is located between said collar and said base shaped like a bell.

13. Syringe as in any of claims 4, 8, or 12, distinguished by the fact that the membrane microfilter is integrated through moulding with one of the bottom of the nozzle, the needle-carrying ferrule, the bracing ferrule, and the collar in the shape of a truncated cone that is attached to the bottom of the nozzle.

14. Syringe as in claim 4 in which the fluid to be injected is put under the pressure of a gas contained in the barrel, distinguished by the fact that the membrane microfilter acts as a barrier to said gas to prevent the passage of said gas through said membrane microfilter after the fluid in the syringe has been injected, the original pressure of said gas being such that once expanded it has a residual pressure less than the bubble point of said membrane microfilter.

15. Syringe as in claim 4, distinguished by the fact that the inner height of the nozzle is at least equal to the outer height of the barrel.

16. Syringe as in claim 4, distinguished by the fact that the useful surface of the filter is less than the smallest straight diameter of the barrel.

* * * * *

UNITED STATES PATENT AND TRADEMARK OFFICE
CERTIFICATE OF CORRECTION

PATENT NO. : 4,596,561

DATED : June 24, 1986

INVENTOR(S) : Meyer et al.

It is certified that error appears in the above-identified patent and that said Letters Patent is hereby corrected as shown below:

Column 4, line 43, "paraticles" should read --particles--.
Column 8, line 37, "ulrasound" should read --ultrasound--.
Column 9, line 50, "1" should read --4--.
Column 9, line 53, "1" should read --4--.
Column 10, line 8, "it" should read --said membrane--.

Signed and Sealed this

Fourteenth Day of October, 1986

[SEAL]

*Attest:*

DONALD J. QUIGG

*Attesting Officer*   *Commissioner of Patents and Trademarks*